United States Patent [19]

Ito et al.

[11] Patent Number: 5,234,722
[45] Date of Patent: Aug. 10, 1993

[54] SOLID ELECTROLYTE FILM, SOLID OXIDE FUEL CELL COMPRISING SUCH A SOLID ELECTROLYTE FILM, AND PROCESSES FOR PRODUCING SUCH FILM AND SOLID OXIDE FUEL CELL

[75] Inventors: Shigenori Ito, Kasugai; Kiyoshi Okumura, Tajimi; Katsuki Yoshioka, Nagoya, all of Japan

[73] Assignee: NGK Insulators, Ltd., Aichi Pref., Japan

[21] Appl. No.: 623,218

[22] Filed: Dec. 6, 1990

[30] Foreign Application Priority Data

Sep. 4, 1990 [JP] Japan .................................. 2-232351

[51] Int. Cl.$^5$ ........................... B05D 1/00; H01M 8/10
[52] U.S. Cl. .................................. 427/453; 427/126.3; 427/376.2; 29/623.5; 429/33
[58] Field of Search ............ 429/33; 427/126.3, 376.2, 427/453; 29/623.5

[56] References Cited

U.S. PATENT DOCUMENTS

| | | | |
|---|---|---|---|
| 3,481,780 | 12/1969 | Mitoff | 427/115 |
| 3,525,646 | 8/1970 | Tannenberger et al. | 429/31 |
| 4,490,444 | 12/1984 | Isenberg | 429/31 |
| 4,614,628 | 9/1986 | Hsu et al. | 264/61 |
| 4,725,346 | 2/1988 | Joshi | 429/30 X |
| 5,051,321 | 9/1991 | Kitagawa et al. | 429/30 |

FOREIGN PATENT DOCUMENTS

| | | |
|---|---|---|
| 0180538 | 5/1986 | European Pat. Off. . |
| 0410420 | 1/1991 | European Pat. Off. . |
| 1488081 | 7/1966 | France . |

*Primary Examiner*—Mark L. Bell
*Assistant Examiner*—Anthony J. Green
*Attorney, Agent, or Firm*—Parkhurst, Wendel & Rossi

[57] ABSTRACT

A solid electrolyte film being formed on a substrate by plasma spraying. The solid electrolyte film has a solid electrolyte structure composed of cerium oxide or zirconium oxide stabilized or partially stabilized with an alkaline earth metal element and/or a rare earth element. The solid electrolyte film has a true porosity of not more than 5%. A solid oxide fuel cell is also disclosed, which involves such a solid electrolyte film being formed on the substrate by plasma spraying, an air electrode provided on one side of the solid electrolyte films and a fuel electrode provided on the other side of the solid electrolyte film. The solid electrolyte film is formed on the substrate by densifying a plasma sprayed solid electrolyte raw film by heating the film in a temperature range of 1,300° to 1,700° C. In the cell, the fuel electrode film or the air electrode is formed onto a surface of the solid electrolyte film.

9 Claims, 4 Drawing Sheets

FIG_1

FIG_2

FIG_3

FIG_4

SOLID ELECTROLYTE FILM, SOLID OXIDE FUEL CELL COMPRISING SUCH A SOLID ELECTROLYTE FILM, AND PROCESSES FOR PRODUCING SUCH FILM AND SOLID OXIDE FUEL CELL

BACKGROUND OF THE INVENTION

1. Field of the Invention

The present invention relates to solid electrolyte films formed on substrates by plasma spraying, solid oxide fuel cells (SOFC) having such films, and processes for producing such films and fuel cells.

2. Related Art Statement

Recently, fuel cells have been noted as power generating devices. The fuel cell is device capable of directly converting chemical energy possessed by fuel to electric energy. Since the fuel cell is free from limitation of Carnot's cycle, the cell is an extremely promising technique in that the fuel cell essentially has a high energy conversion efficiency, a variety of fuels (naphtha, natural gas, methanol, coal reformed gas, heavy oil, etc.) may be used, and the cell provokes less public nuisance, and its power generating efficiency is not influenced by the scale of the equipment.

Particularly, since the solid oxide fuel cell operates at high temperatures of 1,000° C. or more, activity of electrodes is extremely high. Thus, it is not necessary to use catalyst materials of a noble metal such as expensive platinum. In addition, since the SOFC has low polarization and relatively high output voltage, its energy conversion efficiency is conspicuously higher than that in other fuel cells. Furthermore, since their constituent materials are all solid, the SOFC is stable and has long use life.

Although it is desired in the SOFC that the thickness of the solid electrolyte film is made smaller, electrolyte film-forming techniques such as chemical vapor deposition (CVD) or electrochemical vapor deposition (EVD) have problems in that the apparatus becomes large in size, the treated area is too small, and the treating speed is too low.

Plasma spraying has heretofore been used for formation of the solid oxide fuel cells because the plasma spraying has merits in that the film-forming speed is great, the film can be formed simply, thinly and relatively densely (Sunshine 1981, Vol. 2, No. 1).

Further, it is publicly known that after the grain size of a raw material to be plasma sprayed (hereinafter referred to as "plasma spraying raw material"), in which cerium oxide or zirconium oxide is solid solved with an oxide of an alkaline earth metal element or a rare earth element is adjusted, the material is plasma sprayed to form a solid electrolyte film (Japanese patent application Laid-open Nos. 61-198,569 and 61-198,570).

On the other hand, porosity of the solid electrolyte film formed by plasma spraying is generally 5%, and reaches up to 10%, so that such a solid electrolyte film has insufficient density as a solid electrolyte film for SOFC, and cracks or laminar defects occur in the film during the plasma spraying. For this reason, a leakage phenomenon occurs that a fuel such as hydrogen or carbon monoxide penetrates during operation of the SOFC. Consequently, electromotive forces per SOFC is smaller than, for example, 1 V in ordinary fuel cells, so that outputs drop and the conversion rate of the fuel to electric power lowers.

At that time, although it may be considered that the fuel leakage phenomenon is coped with by increasing the thickness of the solid electrolyte film, resistance against diffusion of ions into the bulk in this case becomes greater.

Furthermore, since a number of the laminar defects microstructurally exist as mentioned above, when the conductive solid electrolyte film is formed by plasma spraying, the electric conductivity of the solid electrolyte film is lower than that of a sintered body having the same composition a the solid electrolyte film. Consequently, the internal resistance of the solid oxide fuel cell becomes greater to deteriorate characteristics thereof. Therefore, it is desired that the thickness of the solid electrolyte film itself is decreased to raise outputs of the cell.

SUMMARY OF THE INVENTION

It is an object of the present invention to densify and thin a solid electrolyte film and enhance electric conductivity thereof in the case that the solid electrolyte film is formed on a substrate by plasma spraying.

It is another object of the present invention to apply this densifiable, thinnable plasma sprayed solid electrolyte film to a solid oxide fuel cell, so that outputs of the solid oxide fuel cell may be raised.

A first aspect of the present invention relates to a solid electrolyte film being formed on a substrate by plasma spraying and having a solid electrolyte structure composed of a material selected from cerium oxide or zirconium oxide fully stabilized or partially stabilized with an alkaline earth metal element and/or a rare earth element, wherein the solid electrolyte film has a true porosity of not more than 5%.

A second aspect of the present invention relates to a solid oxide fuel cell comprising: a solid electrolyte film being formed on a substrate by plasma spraying and having a solid electrolyte structure composed of a material selected from cerium oxide or zirconium oxide fully stabilized or partially stabilized with an alkaline earth metal element and/or a rare earth element, wherein the solid electrolyte film has a true porosity of not more than 5%; an air electrode provided on one side of the solid electrolyte film; and a fuel electrode provided on the other side of the solid electrolyte film.

A third aspect of the present invention relates to a process for producing a solid electrolyte film, wherein the process comprises the steps of: preparing a plasma spraying raw material comprising a mixture or a solid solution consisting essentially of an alkaline earth metal element or a rare earth element and cerium oxide or zirconium oxide; forming a plasma sprayed solid electrolyte film on a substrate by plasma spraying the plasma spraying raw material onto the substrate; and densifying the plasma sprayed solid electrolyte film by heating the film in a temperature range of 1,300° to 1,700° C.

A fourth aspect of the present invention relates to a process for producing a solid oxide fuel cell, wherein the process comprises the steps of: preparing a plasma spraying raw material comprising a mixture or a solid solution consisting essentially of an alkaline earth metal element or a rare earth element and cerium oxide or zirconium oxide; forming a plasma sprayed solid electrolyte film on an air electrode by plasma spraying the plasma spraying raw material onto the air electrode; producing a solid electrolyte film by densifying the plasma sprayed solid electrolyte film by heating the film in a temperature range of 1,300° to 1,700° C.; and providing a fuel electrode film to a surface of the solid electrolyte film.

A fifth aspect of the present invention relates to a process for producing a solid oxide fuel cell, wherein the process comprises the steps of: preparing a plasma spraying raw material comprising a mixture or a solid solution consisting essentially of an alkaline earth metal element or a rare earth element and cerium oxide or zirconium oxide; forming a plasma sprayed solid electrolyte film on a fuel electrode by plasma spraying the plasma spraying raw material onto the fuel electrode; producing a solid electrolyte film by densifying the plasma sprayed solid electrolyte film by heating the film in a temperature range of 1,300° to 1,700° C.; and providing an air electrode film on a surface of the solid electrolyte film.

In the present invention, the formation of the solid electrolyte film on the substrate includes a case where the solid electrolyte film is formed on the surface of the substrate and a case where another film, for example, the air electrode film, is formed on the surface of the substrate and then the solid electrolyte film is formed on the surface of another film.

The plasma spraying of the plasma spraying raw material onto the air electrode (or fuel electrode) includes a case where the raw material is plasma sprayed onto the surface of the air electrode film (or fuel electrode film) formed on a surface of a porous substrate and a case where the raw material is plasma sprayed onto the surface of the substrate for the air electrode (or the substrate for the fuel electrode substrate) made of a raw material for the air electrode (or a raw material for the fuel electrode).

The specific solid electrolyte film according to the present invention is formed on the substrate by plasma spraying, and this solid electrolyte film is composed of cerium oxide or zirconium oxide stabilized or partially stabilized with an alkaline earth metal or a rare earth element. Therefore, the solid electrolyte film can be made thinner, and the film-forming speed is high. In addition, although the film is formed by plasma spraying, the true porosity of the film is not more than 5%. Thus, the film has density not seen in the conventional plasma sprayed solid electrolyte films.

These and other objects, features and advantages of the invention will be appreciated upon reading the following description of the invention when taken in conjunction with the attached drawings, with the understanding that some modifications, variations and changes of the same could be made by the skilled person in the art to which the invention pertains without departing from the spirit of the invention or the scope of claims attached hereto.

BRIEF DESCRIPTION OF THE DRAWINGS

For a better understanding of the invention, reference is made to the attached drawings, wherein.

DETAILED DESCRIPTION OF THE INVENTION

In order to produce the solid electrolyte film according to the present invention, the plasma sprayed solid electrolyte film is formed on the substrate, and then the thus formed film s heated in a temperature range of 1,300° to 1,700° C.

Figure 3:
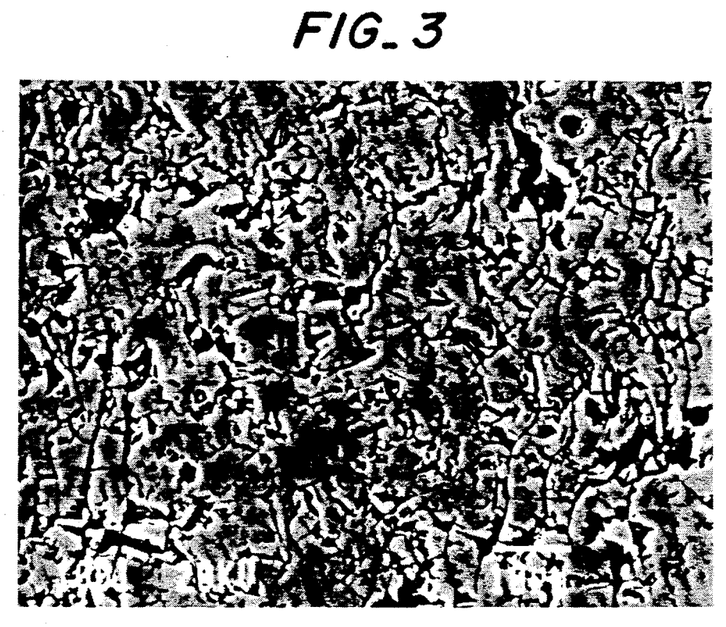
FIGS. 3 and 4 are scanning type electromicroscopic photographs showing the structure of conventional plasma sprayed solid electrolyte films.
Figure 4:
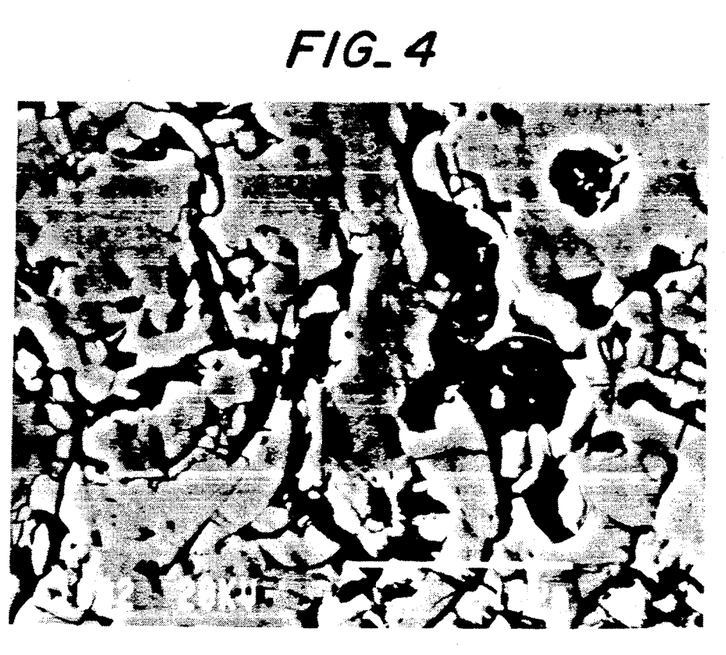

That is, as shown in FIGS. 3 and 4, the microstructure of the conventional plasma sprayed solid electrolyte films having undergone no above heat treatment possess fine cracks or defects peculiar to the plasma sprayed films as well as several layers of laminar defects as shown in FIGS. 3 and 4. This causes a reduction in the electric conductivity and an increase in the gas leakage.

Figure 1:
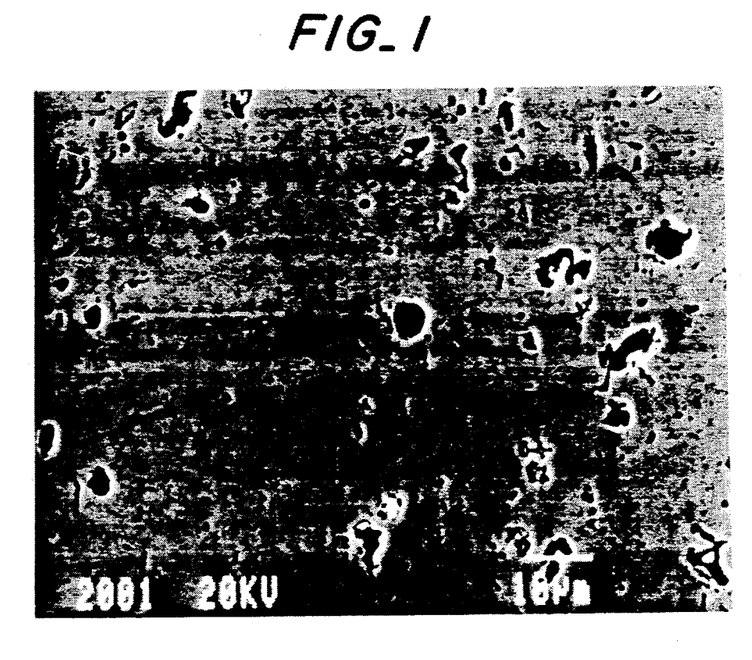
FIGS. 1 and 2 are scanning type electromicroscopic photographs showing the structure of the solid electrolyte films in the Examples according to the present invention.
Figure 2:
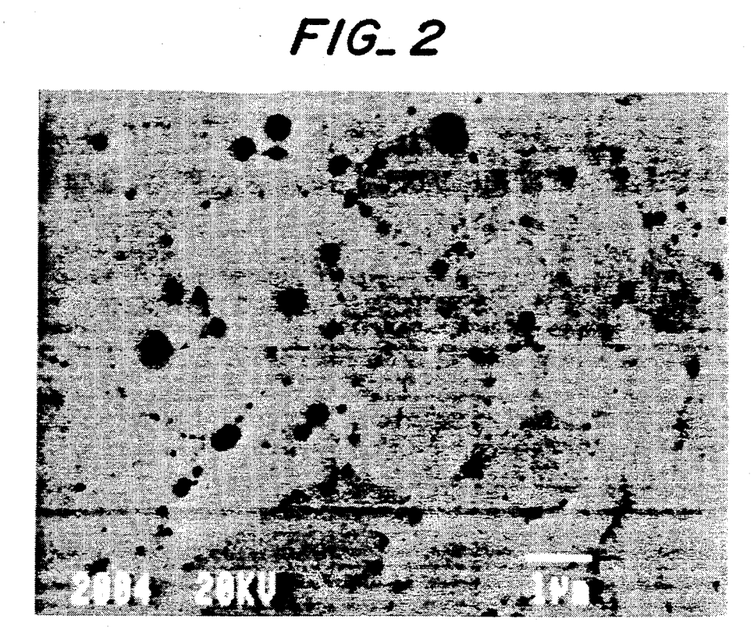

To the contrary, as shown in FIGS. 1 and 2, the solid electrolyte film having undergone the above-mentioned heat treatment is free from microcracks and defects peculiar to the conventional plasma sprayed films, and possesses fewer laminar defects. Since the material moves to acute faces and corners of cleavages of cracks to make the shape of closed pores relatively spheroidal or near spheroidal, the solid electrolyte film has a microstructure near that of the solid electrolyte obtained by press molding powder to obtain a shaped body and then sintering the shaped body, and the composition of the film is homogeneous. As a result, the electric conductivity of the film is equivalent to that of the sintered body, and leakage of gas can be prevented.

Therefore, the solid electrolyte film according to the present invention is useful as a solid electrolyte film for an oxygen sensor and an oxygen densitometer. Further, the film is also useful as an oxidation resistive film for covering metallic materials because of its denseness.

The thus plasma sprayed solid electrolyte can be formed in the form of a thin film, and has high electric conductivity. Therefore, when the film is used as a solid electrolyte for a solid oxide fuel cell, a solid oxide fuel cell having small internal resistance, and capable of generating high output, can be produced.

As compared with EVD as a process for producing a dense thin film solid electrolyte in a conventional solid oxide fuel cell, the present invention is technically simple, and the solid electrolyte film thereof can be formed by using only an ordinary plasma sprayer and an electric furnace or the like for thermal treatment. Thus, the invention has a merit of low cost.

In the case of EVD, although current cylindrical solid oxide fuel cells having relatively small sizes can be produced, it is impossible to produce solid oxide fuel cells having flat shapes. On the other hand, the plasma sprayed solid electrolyte film according to the present invention may be applied to both the flat and cylindrical solid oxide fuel cells. In addition, the solid electrolyte film according to the present invention may easily cop with the production of elongated, cylindrical fuel cells or flat, large area fuel cells in large sizes.

According to the present invention, the open pores in the plasma sprayed solid electrolyte films are converted to closed pores, fine cracks or defects peculiar to the plasma sprayed films can be eliminated, and the true porosity can be reduced to 5% or less. Further, the microstructure of the film can be approached to that of the sintered product, and the composition of the film can be homogenized, so that the electric conductivity of the solid electrolyte can be raised. Therefore, the solid oxide fuel cell produced by the process of the present invention exhibits high electromotive forces, and is stable. Further, since the thickness of the film needs not be increased beyond a necessary level, the internal resistance of the cell is decreased, and outputs greatly rise.

In the production of a plasma sprayed solid electrolyte film, a plasma spraying raw material is a mixture or solid solution of an alkaline earth metal or a rare earth element and cerium oxide or zirconium oxide. Such a raw material is heated at 1300° C.-1700° C. after the plasma spraying.

Preferably, at least one oxide selected from $SiO_2$, $Al_2O_3$ and MgO is added to the mixture or solid solution of alkaline earth metal or rare earth element and cerium oxide or zirconium oxide in a total amount of not less than 0.1 part by weight but not more than 3 parts by weight based on the total weight of the raw material (100 parts by weight), whereby the heat treating temperature can be decreased and the heat treating time can be shortened. Further, the addition of such an oxide in the above amount does not bring about the degradation of properties of the raw material such as electric conductivity o the like from a viewpoint of the material composition. Even in this case, the solid electrolyte film has a structure consisting of cerium oxide or zirconium oxide fully or partially stabilized with the alkaline earth metal or rare earth element.

This raw material is sprayed through plasma spraying such as atmospheric spraying, low pressure spraying or the like. Particularly, the effect is large in the low pressure plasma spraying. Even in the atmospheric plasma spraying, a sufficiently dense plasma sprayed solid electrolyte film can be obtained by the subsequent heat treatment.

Then, the invention will be described with respect to SOFC as a target.

Figure 5:
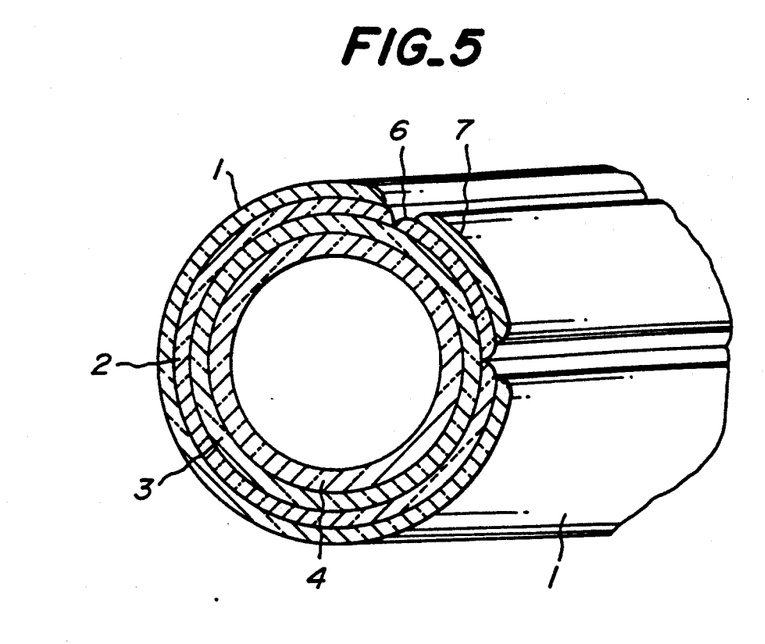
FIG. 5 is a partially broken perspective view of a cylindrical solid electrolyte fuel cell.
Figure 6:
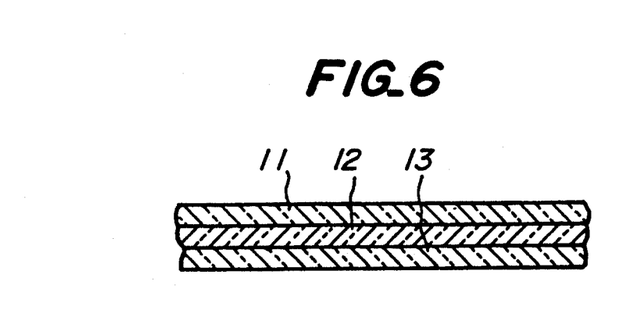
FIG. 6 is a partially sectional view of a flat solid electrolyte fuel cell.

FIG. 5 is a partly broken perspective view of an embodiment of a cylindrical SOFC according to the invention, and FIG. 6 is a partial front view of an embodiment of a flat SOFC according to the invention.

In FIG. 5, an air electrode film 3 is formed on an outer periphery of cylindrical porous ceramic substrate 4, and a solid electrolyte film 2 and a fuel electrode film 1 are arranged around the outer periphery of the electrode film 3 in this order. Furthermore, an interconnector 6 is arranged on the air electrode film 3 at a region of upper side of FIG. 5 and a connecting terminal 7 is attached thereto. In series connection of the cylindrical SOFCs, the air electrode film is connected to the fuel electrode 1 of an adjoining SOFC through the interconnector 6 and the connecting terminal 7. In parallel connection of the cylindrical SOFCs, the fuel electrode films of the adjoining SOFC elements are connected through Ni felt or the like.

The arrangement of the fuel electrode film 1 and the air electrode film 3 may be opposite to the case of FIG. 5. Moreover, a cylindrical air electrode substrate of single layer consisting of an electrode material for the air electrode may be used instead of the air electrode film and the porous substrate 4.

In FIG. 6, a solid electrolyte film 12 is provided on a surface of a flat air electrode substrate 13 made from an air electrode material, and a fuel electrode film 11 is provided on the surface thereof. Moreover, it may be that the solid electrolyte film is provided on a surface of a flat fuel electrode substrate made from a fuel electrode material, and an air electrode film is arranged on the surface thereof.

The air electrode may be made from doped or undoped $LaMnO_3$, $CaMnO_3$, $LaNiO_3$, $LaCoO_3$, $LaCrO_3$ or the like, among which $LaMnO_3$ doped with strontium or calcium is preferable. As the fuel- electrode, nickel-zirconia cermet or cobalt-zirconia cermet is generally preferable.

Moreover, the solid electrolyte film according to the invention is applicable to the flat SOFC and cylindrical SOFC opening at both ends as mentioned above as well as a bag-like cylindrical SOFC sealed at one end.

The following examples are given in illustration of the invention and are not intended as limitations thereof.

EXPERIMENT 1

A slurry was prepared by adding water to a mixed powder consisting of 100 parts by weight of commercially available 8 mol $Y_2O_3$ stabilized $ZrO_2$ powder and 0.2 part by weight of $Al_2O_3$ in an amount of 50 parts by weight based on 100 parts by weight in total of the above mixed powder, which was granulated in a spray drier to prepare granules having an average particle size of 30 μm as a raw material for plasma spraying. Furthermore, various plasma spraying raw materials were prepared as shown in the following Table 1 in the same manner as described above by changing the composition of the components. On the other hand, a flat alumina substrate having a porosity of 20% and a size of 30 long×30 wide×1 thick mm was prepared, to which was sprayed the plasma spraying raw material having a composition shown in Table 1 by means of a plasma sprayer so as to have a thickness of 500 μm. Thereafter, the alumina substrate was polished to obtain an experimental plasma sprayed film of 400 μm in thickness. Such a plasma sprayed film was subjected to a heat treatment in an electric furnace under heat treating conditions shown in Table 1. Then, the composition analysis, true porosity, permeation coefficient of $N_2$ gas and electric conductivity were measured with respect to the resulting solid electrolyte films to obtain results as shown in Table 1.

TABLE 1

| | Composition of starting material for PS (parts by weight) | | | Heat treating conditions | Analysis of PS film composition (parts by weight) | | | True porosity (%) | Permeation coefficient of $N_2$ gas room temperature ($\times 10^{-6}$ cm$^4$ g$^{-1}$s$^{-1}$) | Electric conductivity 1000° C. ($\times 10^{-2}$ S/cm) |
|---|---|---|---|---|---|---|---|---|---|---|
| | $ZrO_2$ | $Y_2O_3$ | $Al_2O_3$ | | $ZrO_2$ | $Y_2O_3$ | $Al_2O_3$ | | | |
| Comparative Example 1-1 | 86.5 | 13.5 | 0 | not treated | 86.4 | 13.2 | 0 | 8.9 | 3.7 | 8 |
| Comparative Example 1-2 | 86.5 | 13.5 | 0 | 1250° C. × 5 hrs | 86.4 | 13.3 | 0 | 7.7 | 3.5 | 9 |
| Example 1-3 | 86.5 | 13.5 | 0 | 1300° C. × 5 hrs | 86.4 | 13.3 | 0 | 5.0 | 2.8 | 11 |

TABLE 1-continued

| | Composition of starting material for PS (parts by weight) | | | Heat treating conditions | Analysis of PS film composition (parts by weight) | | | True porosity (%) | Permeation coefficient of $N_2$ gas room temperature ($\times 10^{-6}$ cm$^4$ g$^{-1}$s$^{-1}$) | Electric conductivity 1000° C. ($\times 10^{-2}$ S/cm) |
|---|---|---|---|---|---|---|---|---|---|---|
| | $ZrO_2$ | $Y_2O_3$ | $Al_2O_3$ | | $ZrO_2$ | $Y_2O_3$ | $Al_2O_3$ | | | |
| Example 1-4 | 86.5 | 13.5 | 0 | 1350° C. × 5 hrs | 86.4 | 13.3 | 0 | 4.7 | 2.8 | 12 |
| Example 1-5 | 86.5 | 13.5 | 0 | 1450° C. × 5 hrs | 86.5 | 13.2 | 0 | 3.5 | 1.4 | 12 |
| Example 1-6 | 86.5 | 13.5 | 0 | 1500° C. × 5 hrs | 86.4 | 13.4 | 0 | 4.1 | 1.7 | 14 |
| Example 1-7 | 86.5 | 13.5 | 0 | 1550° C. × 5 hrs | 86.4 | 13.2 | 0 | 2.4 | 0.3 | 14 |
| Comparative Example 2-1 | 86.5 | 13.5 | 0.2 | not treated | 86.4 | 13.5 | 0.2 | 9.7 | 3.5 | 8 |
| Comparative Example 2-2 | 86.5 | 13.5 | 0.2 | 1250° C. × 5 hrs | 86.4 | 13.4 | 0.2 | 6.7 | 3.5 | 9 |
| Example 2-3 | 86.5 | 13.5 | 0.2 | 1350° C. × 5 hrs | 86.5 | 13.4 | 0.2 | 3.6 | 2.1 | 13 |
| Example 2-4 | 86.5 | 13.5 | 0.2 | 1450° C. × 5 hrs | 86.5 | 13.3 | 0.2 | 3.0 | 0.4 | 14 |
| Example 2-5 | 86.5 | 13.5 | 0.2 | 1500° C. × 5 hrs | 86.4 | 13.3 | 0.2 | 2.1 | 0.6 | 15 |
| Example 2-6 | 86.5 | 13.5 | 0.2 | 1550° C. × 5 hrs | 86.3 | 13.2 | 0.2 | 1.7 | 0.3 | 15 |
| Example 2-7 | 86.5 | 13.5 | 0.2 | 1550° C. × 20 hrs | 86.4 | 13.5 | 0.2 | 1.5 | 0.1 | 15 |
| Comparative Example 3-1 | 94.5 | 5.5 | 3.0 | not treated | 94.5 | 5.5 | 3.1 | 10.1 | 3.3 | 1 |
| Example 3-2 | 94.5 | 5.5 | 3.0 | 1550° C. × 5 hrs | 94.4 | 5.5 | 3.0 | 1.4 | 0.3 | 10 |
| Reference Example 4-1 (sintered body) | 86.5 | 13.5 | 0 | — | 86.4 | 13.6 | 0 | 0.2 | 0 | 15 |

(PS is plasma spraying)

As seen from the examples of Table 1, the true porosity is lowered to not more than 5% through the heat treatment of not lower than 1300° C. In this case, the permeation coefficient of $N_2$ gas rapidly decreases. That is, the permeation coefficient is $3 \times 10^{-6}$ cm$^4$g$^{-1}$s$^{-1}$ to $4 \times 10^{-6}$ cm$^4$g$^{-1}$s$^{-1}$ when the true porosity is more than 5%, but is rapidly decreased to $0.1 \times 10^{-6}$ cm$^4$g$^{-1}$s$^{-1}$ when the true porosity is not more than 5%. Because, when the true porosity is not more than 5%, open pores are substantially removed and only closed pores are existent, and as the temperature rises, these closed pores become smaller.

Furthermore, the electric conductivity rapidly approaches to an electric conductivity of a sintered body of $15 \times 10^{-2}$ s/cm when the true porosity is not more than 5%. This is due to the fact that the open pores are closed to remove laminar cracks and hence disappeared an obstruction resisting to diffusion of oxygen no longer exits.

As shown in Examples 2-3 through 2-7, the true porosity is smaller in a case of adding $Al_2O_3$ than in a case of adding no $Al_2O_3$ even at the same heat treating temperature, so that the effect through the heat treatment is larger as compared with that in the case of adding no $Al_2O_3$. On the other hand, the addition of $Al_2O_3$ has a small effect on the electric conductivity. However, when $Al_2O_3$ is added in an amount of 3 parts by weight, the electric conductivity is 10 s/cm under conditions of 1550° C.×5 hours and is fairly smaller as compared with that in the case of adding no $Al_2O_3$ but becomes substantially equal to 8-9 s/cm in Comparative Examples 1-1 to 1-2 having undergone not heat treatment. Therefore, the addition of $Al_2O_3$ in an amount larger than 3 parts by weight has an effect on the densification but causes the large degradation of electric conductivity, so that it is unsuitable for use in fuel cell or the like.

The observation results of microstructure in solid electrolyte films was observed through scanning type electron microscope (SEM), and results are shown in FIGS. 1-4 by photographs, wherein FIGS. 1 and 2 correspond to Example 2-6 and FIGS. 3 and 4 correspond to Comparative Example 2-1.

As seen from SEM photographs, in the solid electrolyte film according to the invention, laminar defects (gap) and cracks inherent to the plasma sprayed film are not observed, and also the shape of closed pores is near to spherical.

The measurement of each property is described as follows.

TRUE POROSITY

True Porosity was determined according to an equation of $(1-(\rho 1/\rho 2)) \times 100\%$ from a bulk $\rho 1$ measured by an Archimedian method and a theoretical density $\rho 2 = 5.96$ calculated by using a lattice constant $d = 5.14$ angstroms through X-ray diffraction (in case of adding 13.5 parts by weight of $Y_2O_3$).

In case of 5.5 parts by weight of $Y_2O_3$ added, it was calculated from a true specific gravity $\rho 2 = 5.90$ measured by means of a pycnometer.

PERMEATION COEFFICIENT OF $N_2$ GAS

Figure 7:
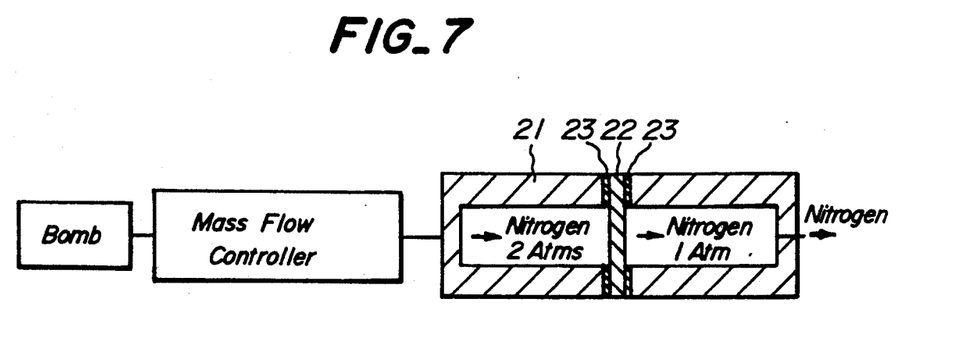
FIG. 7 is a sectional diagram illustrating a method for measuring an $N_2$ permeation coefficient.

As shown in FIG. 7, the solid electrolyte film 22 shown in Table 1 was set to a jig 21 and a gap between the film 22 and the jig 21 was sealed with an adhesive 23.

A side face of the solid electrolyte film 22 was exposed to a nitrogen atmosphere of 2 atmospheric pressure, and the other side face was exposed to a nitrogen atmosphere of an atmospheric pressure (measured at room temperature). In this case, a flow rate of $N_2$ from 2 atmospheric pressure side to 1 atmospheric pressure side was measured by means of a mass flow controller, from which the permeation coefficient K (cm$^4$g$^{-1}$s$^{-1}$) of $N_2$ gas was calculated according to the following equation:

$$K = (t \cdot Q)/(\Delta P \cdot A)$$

where
t: thickness of sample (cm)
Q: measured flow rate (cm$^3$/s)
$\Delta P$: pressure difference (g/cm$^2$)
A: opening area (cm$^2$)

ELECTRIC CONDUCTIVITY

The plasma sprayed film shown in Table 1 was cut into a specimen of 14 mm in diameter and 0.4 mm in thickness and the electric conductivity of the specimen was measured by an alternating current impedance method using a platinum electrode (measured in air at a temperature of 1000° C.).

EXPERIMENT 2

A slurry was prepared by adding water to a mixed powder consisting of 100 parts by weight of commercially available 8 mol $Y_2O_3$ stabilized $ZrO_2$ powder and 0.3 part by weight of $Al_2O_3$ in an amount of 50 parts by weight based on 100 parts by weight in total of the above mixed powder, which was granulated in a spray drier to prepare granules having an average particle size of 30 μm as a raw material for plasma spraying. Furthermore, various spraying materials shown in the following Table 2 were prepared in the same manner as described above by changing the composition of the components. On the other hand, a disc-like $La_{0.9}Sr_{0.1}MnO_3$ substrate having a porosity of 20% and a size of 30×1 mm and a zirconia cermet substrate stabilized with nickel and yttria were provided, to which was sprayed the plasma spraying raw material having the composition shown in Table 2 by means of a plasma sprayer so as to have a thickness of 200 μm.

Thereafter, each of the sprayed solid electrolyte films was subjected to a heat treatment under heat treating conditions shown in Table 2. A platinum paste was applied onto the surface of the resulting solid electrolyte film to produce an SOFC, which was operated at 1000° C. in a hydrogen-oxygen atmosphere to measure an electromotive force. In case of using $La_{0.9}Sr_{0.1}MnO_3$ substrate, the side of $La_{0.9}Sr_{0.1}MnO_3$ was an air electrode (oxygen-side electrode) and platinum side was a fuel electrode (hydrogen-side electrode), while in case of using nickel-yttria stabilized zirconia substrate, platinum side was an air electrode (oxygen-side electrode) and the substrate side was a fuel electrode (hydrogen-side electrode).

Electromotive forces were measured, and results are shown in Table 2. Furthermore, electromotive forces were measured on an SOFC formed by applying a platinum paste to both surfaces of a yttria-stabilized zirconia sintered body (30 mm in diameter × 1 mm in thickness), and results are also shown in Table 2. In the latter case, platinum was used for each of the air and fuel electrodes.

TABLE 2(a)

| | Composition of starting material for PS (parts by weight) | | | | | Substrate for plasma spraying | Heat treating conditions | Measurement of electromotive force (V) |
|---|---|---|---|---|---|---|---|---|
| | $ZrO_2$ | $Y_2O_3$ | $Al_2O_3$ | $SiO_2$ | MgO | | | |
| Comparative Example 1-1 | 86.4 | 13.6 | — | — | — | $La_{0.9}Sr_{0.1}MnO_3$ | not treated | 0.90 |
| Example 1-2 | 86.4 | 13.6 | — | — | — | $La_{0.9}Sr_{0.1}MnO_3$ | 1300° C. × 5 hrs | 1.05 |
| Example 1-3 | 86.4 | 13.6 | — | — | — | $La_{0.9}Sr_{0.1}MnO_3$ | 1450° C. × 5 hrs | 1.09 |
| Example 1-4 | 86.4 | 13.6 | — | — | — | $La_{0.9}Sr_{0.1}MnO_3$ | 1600° C. × 5 hrs | 1.09 |
| Comparative Example 1-5 | 86.4 | 13.6 | — | — | — | $La_{0.9}Sr_{0.1}MnO_3$ | 1750° C. × 5 hrs | measurement impossible |
| Comparative Example 2-1 | 86.4 | 13.6 | 0.3 | — | — | $La_{0.9}Sr_{0.1}MnO_3$ | not treated | 0.89 |
| Example 2-2 | 86.4 | 13.6 | 0.3 | — | — | $La_{0.9}Sr_{0.1}MnO_3$ | 1300° C. × 5 hrs | 1.08 |
| Example 2-3 | 86.4 | 13.6 | 0.3 | — | — | $La_{0.9}Sr_{0.1}MnO_3$ | 1450° C. × 5 hrs | 1.10 |
| Example 2-4 | 86.4 | 13.6 | 0.3 | — | — | $La_{0.9}Sr_{0.1}MnO_3$ | 1600° C. × 5 hrs | 1.11 |
| Comparative Example 3-1 | 86.4 | 13.6 | — | 0.5 | — | $La_{0.9}Sr_{0.1}MnO_3$ | not treated | 0.88 |
| Example 3-2 | 86.4 | 13.6 | — | 0.5 | — | $La_{0.9}Sr_{0.1}MnO_3$ | 1300° C. × 5 hrs | 1.07 |
| Example 3-3 | 86.4 | 13.6 | — | 0.5 | — | $La_{0.9}Sr_{0.1}MnO_3$ | 1450° C. × 5 hrs | 1.12 |
| Example 3-4 | 86.4 | 13.6 | — | 0.5 | — | $La_{0.9}Sr_{0.1}MnO_3$ | 1600° C. × 5 hrs | 1.10 |

TABLE 2(b)

| | Composition of starting material for PS (parts by weight) | | | | | Substrate for plasma spraying | Heat treating conditions | Measurement of electromotive force (V) |
|---|---|---|---|---|---|---|---|---|
| | $ZrO_2$ | $Y_2O_3$ | $Al_2O_3$ | $SiO_2$ | MgO | | | |
| Comparative Example 4-1 | 86.4 | 13.6 | 0.5 | — | 0.5 | Ni—YSZ | not treated | 0.89 |
| Example 4-2 | 86.4 | 13.6 | 0.5 | — | 0.5 | Ni—YSZ | 1300° C. × 5 hrs | 1.09 |
| Example 4-3 | 86.4 | 13.6 | 0.5 | — | 0.5 | Ni—YSZ | 1450° C. × 5 hrs | 1.09 |
| Example 4-4 | 86.4 | 13.6 | 0.5 | — | 0.5 | Ni—YSZ | 1600° C. × 5 hrs | 1.10 |
| Example 4-5 | 56.4 | 13.6 | — | — | 0.5 | Ni—YSZ | 1700° C. × 5 hrs | 1.10 |
| Comparative Example 5-1 | 86.4 | 13.6 | — | — | 2.0 | Ni—YSZ | not treated | 0.89 |
| Example 5-2 | 86.4 | 13.6 | — | — | 2.0 | Ni—YSZ | 1300° C. × 5 hrs | 1.09 |
| Example 5-3 | 86.4 | 13.6 | — | — | 2.0 | Ni—YSZ | 1450° C. × 5 hrs | 1.11 |
| Example 5-4 | 86.4 | 13.6 | — | — | 2.0 | Ni—YSZ | 1600° C. × 5 hrs | 1.10 |
| Reference Example 6-1 (sintered body) | 86.5 | 13.5 | — | — | — | — | — | 1.10 |

(Ni—YSZ is nickel—yttria stabilized zirconia)

As seen from Table 2, the electromotive force is not less than 1.00 V in the heat treatment of 1300° C. Furthermore, the electromotive force is near or equal to that in the sintered body of 1.10 V in the heat treatment of 1450°–1700° C. At a temperature of higher than 1700°

C., deformation and cracking occurred in the heat treated sample, so that the measurement of the electromotive forces was impossible. That is, when the heating temperature exceeds 1700° C., the heat influence on the laminate of the substrate and the $Y_2O_3$ stabilized zirconia is so large that the cell loses strength as a laminate and the deformation and cracking occurs. Thus, it can be seen that the such a cell can not be put into practical use.

MEASUREMENT OF ELECTROMOTIVE FORCE

Figure 8:
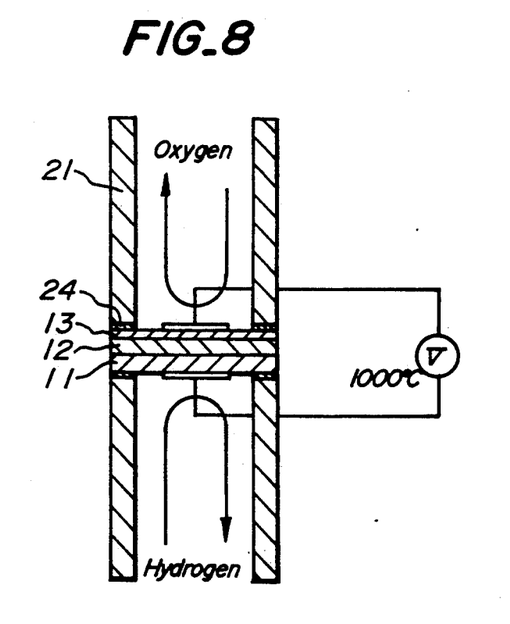
FIG. 8 is a sectional diagram illustrating a method for measuring electromotive forces

As shown in FIG. 8, oxygen was supplied to a side of the air electrode 13 in an SOFC of 30 mm in diameter, while hydrogen was supplied to a side of the fuel electrode 11. The gap between SOFC and jig 21 was sealed with a glass sealing material 24. Then, the electromotive force was measured by operating the SOFC at a temperature of 1000° C.

What is claimed is:

1. A solid electrolyte film formed on a substrate consisting essentially of $LaMnO_3$ by plasma spraying and then heat treating at 1300°–1700° C., said solid electrolyte film consisting of zirconium oxide stabilized or partially stabilized with at least one element selected from the group consisting of alkaline earth metal elements and rare earth elements, said solid electrolyte film having a true porosity of not more than 5%.

2. A solid oxide fuel cell comprising:
   an air electrode consisting essentially of $LaMnO_3$;
   a solid electrolyte film formed on said air electrode by plasma spraying and then heat treating at 1300°–1700° C., said solid electrolyte film consisting of zirconium oxide stabilized or partially stabilized with at least one element selected from the group consisting of alkaline earth metal elements and rare earth elements, said solid electrolyte film having a true porosity of not more than 5%; and
   a fuel electrode providing on a side of said solid electrolyte film opposite said air electrode.

3. A process for producing a solid electrolyte film on a substrate consisting essentially of $LaMnO_3$, said process comprising the steps of:
   preparing a raw material to be plasma sprayed, said raw material containing a mixture or a solid solution consisting of zirconium oxide stabilized or partially stabilized with at least one element selected from the group consisting of alkaline earth metal elements and rare earth elements;
   forming a plasma sprayed solid electrolyte film on a surface of said substrate by plasma spraying said raw material onto said surface; and
   heat treating said plasma sprayed solid electrolyte film in a temperature range of 1,300° to 1,700° C.

4. A process for producing a solid oxide fuel cell, said process comprising the steps of:
   preparing a raw material to be plasma sprayed, said plasma spraying raw material containing a mixture or a solid solution consisting of zirconium oxide stabilized or partially stabilized with at least one element selected from the group consisting of alkaline earth metal elements and rare earth elements;
   preparing an air electrode consisting essentially of $LaMnO_3$;
   forming a plasma sprayed solid electrolyte film on said air electrode by plasma spraying said raw material onto said air electrode;
   heat treating said plasma sprayed solid electrolyte film in a temperature range of 1,300° to 1,700° C.; and
   providing a fuel electrode film on a surface of the solid electrolyte film opposite said air electrode.

5. The solid oxide fuel cell of claim 2, wherein said air electrode is a substrate for the solid electrolyte film and fuel electrode provided thereon.

6. The solid electrolyte film of claim 1, wherein said $LaMnO_3$ is doped with at least one of Sr and Ca.

7. The solid oxide fuel cell of claim 2, wherein said $LaMnO_3$ is doped with at least one of Sr and Ca.

8. The process of claim 3, wherein said $LaMnO_3$ is doped with at least one of Sr and Ca.

9. The process of claim 4, wherein said $LaMnO_3$ is doped with at least one of Sr and Ca.

* * * * *